(12) United States Patent
Prokop

(10) Patent No.: US 11,871,950 B2
(45) Date of Patent: Jan. 16, 2024

(54) TISSUE RESECTING DEVICE INCLUDING A MOTOR COOLING ASSEMBLY

(71) Applicant: Covidien LP, Mansfield, MA (US)

(72) Inventor: Paul F. Prokop, Woburn, MA (US)

(73) Assignee: Covidien LP, Mansfield, MA (US)

( * ) Notice: Subject to any disclaimer, the term of this patent is extended or adjusted under 35 U.S.C. 154(b) by 562 days.

(21) Appl. No.: 17/143,601

(22) Filed: Jan. 7, 2021

(65) Prior Publication Data

US 2021/0121194 A1 Apr. 29, 2021

Related U.S. Application Data

(62) Division of application No. 16/284,537, filed on Feb. 25, 2019, now Pat. No. 10,898,218.

(51) Int. Cl.
*A61B 17/32* (2006.01)
*A61B 17/00* (2006.01)
(Continued)

(52) U.S. Cl.
CPC ............... *A61B 17/320016* (2013.01); *A61B 17/00234* (2013.01); *A61B 18/1442* (2013.01);
(Continued)

(58) Field of Classification Search
CPC ............ B25F 5/008; A61B 17/320016; A61B 17/00234; A61B 18/1442;
(Continued)

(56) References Cited

U.S. PATENT DOCUMENTS

| 1,585,934 A | 5/1926 | Muir |
| 1,666,332 A | 4/1928 | Hirsch |

(Continued)

FOREIGN PATENT DOCUMENTS

| EP | 1753350 B1 | 8/2014 |
| WO | 2015023965 A1 | 2/2015 |

OTHER PUBLICATIONS

Extended European Search Report issued in application No. 17183474.0 dated Nov. 6, 2017.

*Primary Examiner* — Christopher M Koehler
*Assistant Examiner* — Riley Owen Stout
(74) *Attorney, Agent, or Firm* — Carter, DeLuca & Farrell LLP (57) ABSTRACT

A tissue resecting device includes a handpiece assembly and an end effector assembly. The handpiece assembly includes a motor and a cooling assembly. The cooling assembly includes a housing, a fan assembly, and a fin pack. The fan assembly includes a tubular member configured to be received in the elongate cover, and a plurality of blades rotatably supported on the tubular member and operatively coupled with a drive rotor of the motor for concomitant rotation therewith. The fin pack includes a tubular base and a plurality of fins extending radially outward from the tubular base. The tubular base is disposed within the elongate cover and about the tubular member of the fan assembly. Actuation of the motor rotates the plurality of blades of the fan assembly to thereby advance air through a space between the fin pack and the elongate cover of the housing to facilitate cooling of the motor.

19 Claims, 3 Drawing Sheets

(51) Int. Cl.
   *B25F 5/00*  (2006.01)
   *A61B 18/14* (2006.01)
(52) U.S. Cl.
   CPC .............. *A61B 2017/00296* (2013.01); *A61B 2017/32007* (2017.08); *B25F 5/008* (2013.01)
(58) Field of Classification Search
   CPC ........... A61B 2017/00296; A61B 2017/32007; A61B 2017/4216; A61B 17/32002; H02K 5/20; H02K 5/10
   See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Vans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |

(56) References Cited

U.S. PATENT DOCUMENTS

| | | |
|---|---|---|
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,171,316 B1 | 1/2001 | Kovac et al. |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,663,641 B1 | 12/2003 | Kovac et al. |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,062,214 B2 | 11/2011 | Shener et al. |
| 8,419,626 B2 | 4/2013 | Shener-Irmakoglu et al. |
| 8,574,253 B2 | 11/2013 | Gruber et al. |
| 8,663,264 B2 | 3/2014 | Cesarini et al. |
| 8,678,999 B2 | 3/2014 | Isaacson |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 10,765,486 B2 | 9/2020 | Bajo et al. |
| 10,898,218 B2 | 1/2021 | Prokop |
| 11,179,172 B2* | 11/2021 | Wood ............. A61B 17/32002 |
| 2001/0039963 A1 | 11/2001 | Spear et al. |
| 2001/0047183 A1 | 11/2001 | Privitera et al. |
| 2002/0040229 A1* | 4/2002 | Norman .......... A61B 17/32002 |
| | | 606/180 |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2003/0225344 A1 | 12/2003 | Miller |
| 2004/0010258 A1 | 1/2004 | Carusillo et al. |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2005/0277970 A1 | 12/2005 | Norman et al. |
| 2006/0036132 A1 | 2/2006 | Renner et al. |
| 2006/0047185 A1 | 3/2006 | Shener et al. |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0093764 A1* | 4/2009 | Pfeffer ................. A61M 60/82 |
| | | 604/151 |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0125287 A1 | 5/2010 | Cole et al. |
| 2010/0152647 A1 | 6/2010 | Shener et al. |
| 2011/0166419 A1 | 7/2011 | Reif et al. |
| 2012/0078038 A1 | 3/2012 | Sahney et al. |
| 2012/0150179 A1* | 6/2012 | Feinberg ............ A61B 18/1445 |
| | | 606/48 |
| 2013/0060270 A1 | 3/2013 | Teeslink et al. |
| 2013/0131452 A1 | 5/2013 | Kuroda et al. |
| 2013/0304069 A1* | 11/2013 | Bono ................. A61B 17/1671 |
| | | 606/80 |
| 2014/0031834 A1 | 1/2014 | Germain et al. |
| 2018/0168757 A1 | 6/2018 | Bono |
| 2018/0177540 A1* | 6/2018 | Lepoutre .......... A61B 17/8836 |
| 2019/0273421 A1* | 9/2019 | Velderman ............... H02K 5/18 |

* cited by examiner

TISSUE RESECTING DEVICE INCLUDING A MOTOR COOLING ASSEMBLY

CROSS REFERENCE TO RELATED APPLICATIONS

This application is a divisional application of U.S. patent application Ser. No. 16/284,537, filed on Feb. 25, 2019. The entire contents of the foregoing application are hereby incorporated by reference herein.

BACKGROUND

Technical Field

The present disclosure relates generally to the field of tissue resection. In particular, the present disclosure relates to a tissue resecting device including a cooling assembly.

Background of Related Art

Tissue resection may be performed endoscopically within an organ, such as a uterus, by inserting an endoscope (or hysteroscope) into the uterus and passing a tissue resection device through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space. Such fluid may be used to provide cooling to mechanical or electro-mechanical parts in the tissue resection device. However, such practice requires extensive sterilization of the tissue resection device.

SUMMARY

As used herein, the term "distal" refers to the portion that is described which is farther from a user, while the term "proximal" refers to the portion that is described which is closer to a user. Further, to the extent consistent, any or all of the aspects described herein may be used in conjunction with any or all of the other aspects described herein.

In accordance with an aspect of the present disclosure, a tissue resecting device includes a handpiece assembly and an end effector assembly. The handpiece assembly includes a motor and a cooling assembly. The cooling assembly includes a housing, a fan assembly, and a fin pack. The housing includes an elongate cover defining a first lumen therethrough. The fan assembly includes a tubular member configured to be received in the first lumen of the elongate cover of the housing, and a plurality of blades rotatably supported on the tubular member and operatively coupled with a drive rotor of the motor for concomitant rotation therewith. The fin pack includes a tubular base and a plurality of fins extending radially outward from the tubular base. The tubular base is disposed within the elongate cover and about the tubular member of the fan assembly. The end effector assembly includes a proximal hub housing and a cutting member extending distally from the proximal hub housing and operatively coupled to the drive rotor of the motor. Actuation of the motor rotates the cutting member and the plurality of blades of the fan assembly to thereby advance air through a space between the fin pack and the elongate cover of the housing to facilitate cooing of the motor.

In an aspect, the housing may further include an adapter portion configured to receive a portion of the end effector assembly therein.

In another aspect, the cooling assembly may further include a heat transfer member thermally coupled with the motor. The heat transfer member may include a tubular portion configured to be supported about the tubular member of the fan assembly, and an outer portion extending distally from the tubular portion.

In yet another aspect, the tubular portion of the heat transfer member may be disposed within the elongate cover of the housing, and the outer portion may be external to the elongate cover.

In still yet another aspect, the housing may further include fingers extending distally from the elongate cover such that when the tubular portion of the heat transfer member is received within the elongate cover, the outer portion of the heat transfer member engages the fingers and defines an opening configured to discharge air therethrough.

In an aspect, each fin of the fin pack may extend at least the length of the tubular base.

In another aspect, at least a portion of each fin of the fin pack may be in communication with the opening defined between the elongate cover and the outer portion of the heat transfer member.

In yet another aspect, at least one fin of the plurality of fins of the fin pack may engage the outer portion of the heat transfer member such that the at least one fin is thermally coupled with the outer portion.

In still yet another aspect, at least one fin of the plurality of fins of the fin pack may be in communication with a slot defined between the adapter portion and the elongate cover of the housing.

In another aspect, the outer portion of the fan assembly may have an annular configuration.

In still another aspect, the housing may be formed of at least one of plastic or metal.

In an aspect, at least one of the plurality of fins of the fin pack may extend distally from the tubular base.

In yet another aspect, the at least one of the plurality of fins of the fin pack may define a gap with the tubular member of the fan assembly.

In accordance with another aspect of the present disclosure, a handpiece assembly for use with a tissue resecting device includes a motor including a drive rotor, and a cooling assembly. The cooling assembly includes a housing, a fan assembly, a heat transfer member, and a fin pack. The housing includes an adapter portion and an elongate cover extending proximally from the adapter portion. The housing defines a first slot between the adapter portion and the elongate cover. The fan assembly includes a tubular member dimensioned to be received in the elongate cover of the housing, and a plurality of blades operatively coupled with the drive rotor of the motor for concomitant rotation therewith. The heat transfer member is disposed about the tubular member of the fan assembly. The heat transfer member is thermally coupled with the motor. The fin pack includes a tubular base supported about the heat transfer member, and a plurality of fins circumferentially arranged about the tubular base. Actuation of the motor advances air through a space between the elongate cover and the fin pack.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Figure 1:
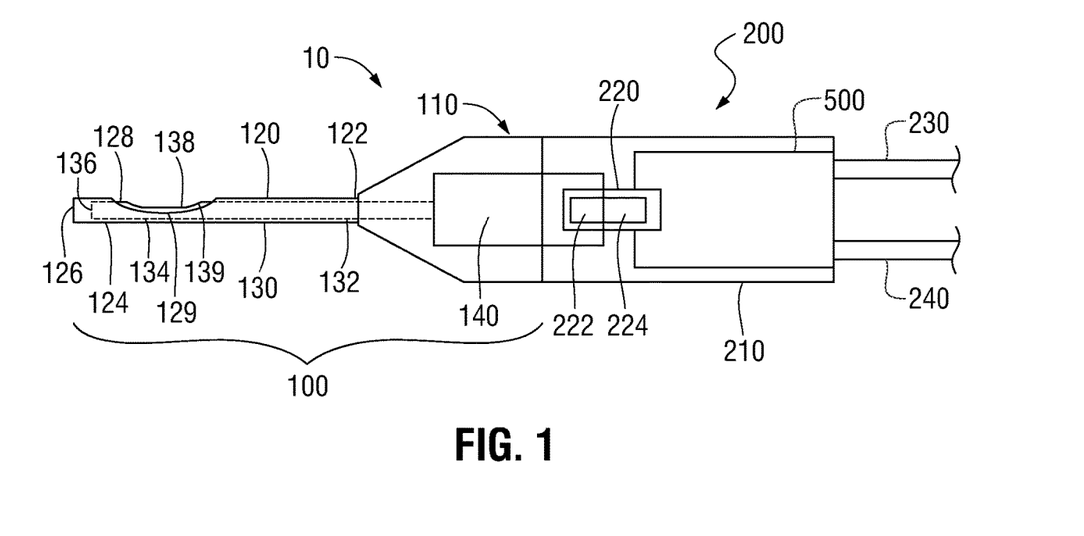
FIG. 1 is a side view of a tissue resecting device in accordance with an aspect of the present disclosure.

Referring generally to FIG. 1, a tissue resecting device 10 provided in accordance with the present disclosure and configured to resect tissue includes an end effector assembly 100 and a handpiece assembly 200. Tissue resecting device 10 is adapted to connect to a control unit (not shown), e.g., via cable 230, to provide power and control functionality to tissue resecting device 10, although tissue resecting device 10 may alternatively or additionally include controls associated with handpiece assembly 200 and/or a power source, e.g., battery, disposed within handpiece assembly 200. In other embodiments, tissue resecting device 10 is manually powered and/or controlled. Tissue resecting device 10 is further adapted to connect to a fluid management system (not shown), e.g., via outflow tubing 240, for removing fluid, tissue, and debris from a surgical site via tissue resecting device 10. The control unit and fluid management system may be integral with one another, coupled to one another, or separate from one another.

With continued reference to FIG. 1, tissue resecting device 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In either of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies with handpiece assembly 200.

End effector assembly 100 includes a proximal hub housing 110, an elongated outer shaft 120 fixedly engaged with and extending distally from proximal hub housing 110, an inner cutting shaft 130 movably disposed within elongated outer shaft 120, and an inner drive core 140. Inner drive core 140 is operably disposed within proximal hub housing 110 and coupled to inner cutting shaft 130 such that rotational input imparted to inner drive core 140, e.g., via handpiece assembly 200, drives rotation of inner cutting shaft 130 within and relative to elongated outer shaft 120. In embodiments, inner cutting shaft 130 may be configured to additionally or alternatively reciprocate relative to elongated outer shaft 120.

Proximal hub housing 110 of end effector assembly 100 is configured to releasably engage handle housing 210 of handpiece assembly 200, e.g., via snap-fit, threaded, luer-lock, lock-button, or other suitable engagement, and may be configured for fixed engagement with handle housing 210 or rotational engagement therewith. Handle housing 210 may be formed of metal, plastic, or combination thereof.

Figure 2:
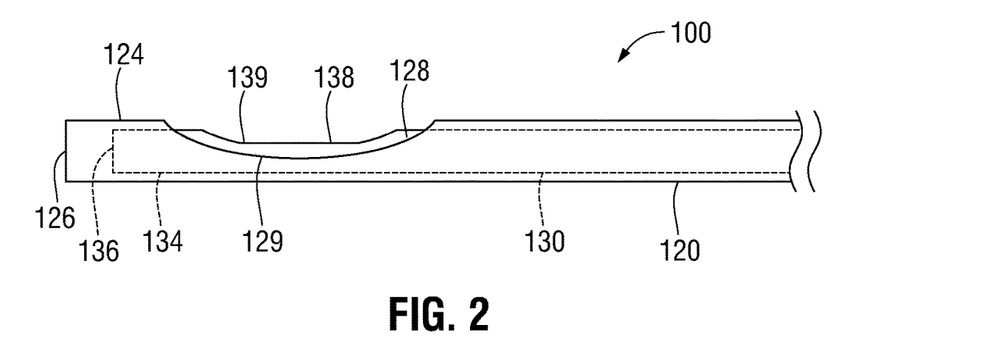
FIG. 2 is a side view of a distal end portion of an end effector assembly of the tissue resecting device of FIG. 1, disposed in an open position.
Figure 3:
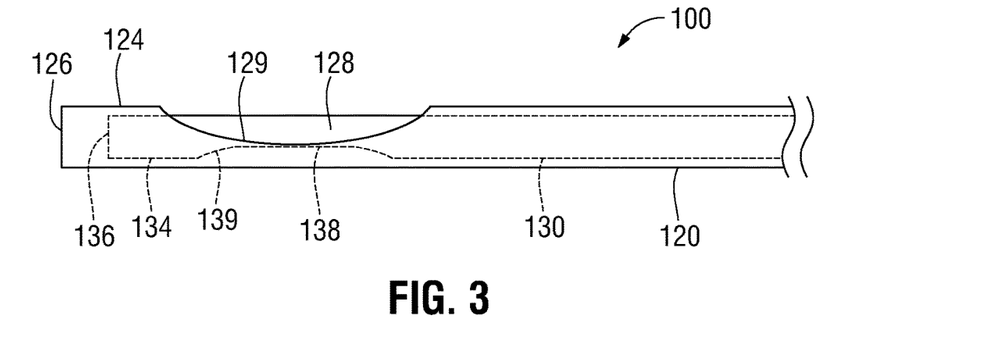
FIG. 3 is a side view of the distal end portion of the end effector assembly of the tissue resecting device of FIG. 1, disposed in a closed position.

Referring also to FIGS. 2 and 3, elongated outer shaft 120 of end effector assembly 100 includes a proximal end portion 122 extending into and fixedly engaged within proximal hub housing 110. Elongated outer shaft 120 extends distally from proximal hub housing 110 to distal end portion 124 defining a closed distal end 126 and a window 128 proximally-spaced from closed distal end 126. Window 128 provides access to the interior of elongated outer shaft 120 and may be surrounded by a cutting edge 129 about the outer perimeter of window 128 so as to facilitate cutting of tissue passing through window 128 and into elongated outer shaft 120. Alternatively, edge 129 may be blunt.

Inner cutting shaft 130 includes a proximal end portion 132 and a distal end portion 134 defining a closed distal end 136 and a window 138 proximally-spaced from closed distal end 136. The edge of inner cutting shaft 130 surrounding window 138 defines a cutting blade 139 to facilitate cutting of tissue passing through window 138 and into inner cutting shaft 130. Inner cutting shaft 130 is rotatable relative to elongated outer shaft 120. Inner cutting shaft 130 may be continuously rotated in a single direction or may be configured to reverse and move in opposite directions. In either configuration, rotation of inner cutting shaft 130 relative to elongated outer shaft 120 defines at least one open position of end effector assembly 100 (see FIG. 2), wherein inner cutting shaft 130 is oriented relative to elongated outer shaft 120 such that window 138 at least partially overlaps window 128, thus enabling fluid communication therebetween, and at least one closed position of end effector assembly 100 (see FIG. 3), wherein inner cutting shaft 130 is oriented relative to elongated outer shaft 120 such that window 138 does not radially overlap window 128, thus inhibiting fluid communication therebetween. In the at least one open position, cutting blade 139 is exposed; in the at least one closed position, cutting blade 139 is not exposed.

Referring back to FIG. 1, inner drive core 140 of end effector assembly 100 may include a generally cylindrical body defining a lumen extending longitudinally therethrough. At least a portion of the lumen defines a non-circular cross-section. The inner drive core 140 extends proximally from proximal hub housing 110 of end effector assembly 100 and is configured to engage distal drive rotor 222 of a drive assembly 220. At least a portion of distal drive rotor 222 defines a non-circular cross-section that is complementary to that of the lumen of inner drive core 140 such that engagement of distal drive rotor 222 with inner drive core 140 rotationally fixes distal drive rotor 222 with inner drive core 140. In addition, inner drive core 140 extends distally through proximal hub housing 110 and is (directly or indirectly) fixedly engaged with proximal end portion 132 of inner cutting shaft 130 within proximal hub housing 110. Under such a configuration, rotation of inner drive core 140 imparts rotation to inner cutting shaft 130. Thus, with end effector assembly 100 engaged with handpiece assembly 200, motor 224 may be activated to drive rotation of distal drive rotor 222, thereby driving rotation of inner cutting shaft 130 relative to elongated outer shaft 120.

Handpiece assembly 200 generally includes a handle housing 210, a drive assembly 220 disposed within handle housing 210, a cooling assembly 500 operatively coupled with the drive assembly 220, a cable 230, and an outflow tubing 240. Handle housing 210, as detailed above, is configured to releasably engage proximal hub housing 110 of end effector assembly 100, and defines a pencil-grip configuration, although other configurations are also contemplated, e.g., a pistol-grip configuration. Handpiece assembly 200 may further include one or more controls (not shown) disposed on or operably associated with handle housing 210 to facilitate activation of drive assembly 220 in a desired manner.

Drive assembly 220 includes a distal drive rotor 222 and a motor 224 that drives rotation of distal drive rotor 222. Distal drive rotor 222 is configured to mate with inner drive core 140 of end effector assembly 100 upon engagement of end effector assembly 100 with handpiece assembly 200 to thereby engage distal drive rotor 222 and inner drive core 140 with one another. Cable 230 provides power and/or control signals to motor 224 to control rotation of distal drive rotor 222.

Figure 4:
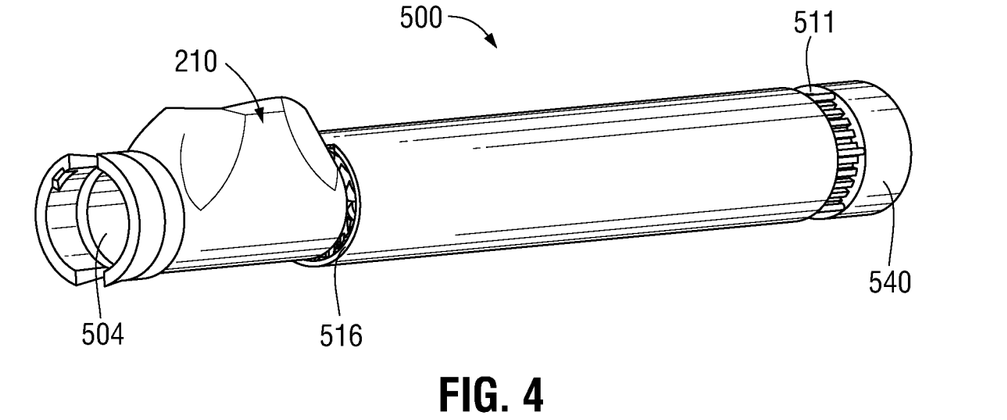
FIG. 4 is a cooling assembly of the handpiece assembly in accordance with an aspect of the present disclosure.
Figure 5:
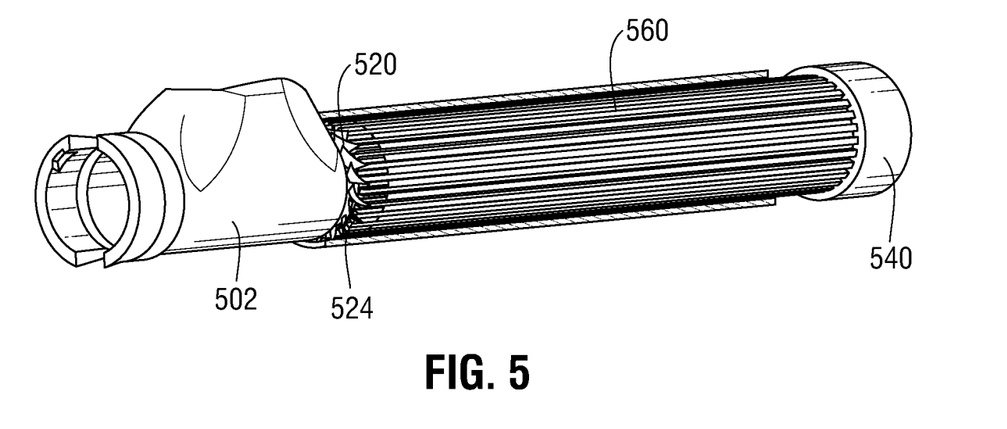
FIG. 5 is a partial perspective view of the cooling assembly of FIG. 4 with an elongate cover removed.
Figure 6:
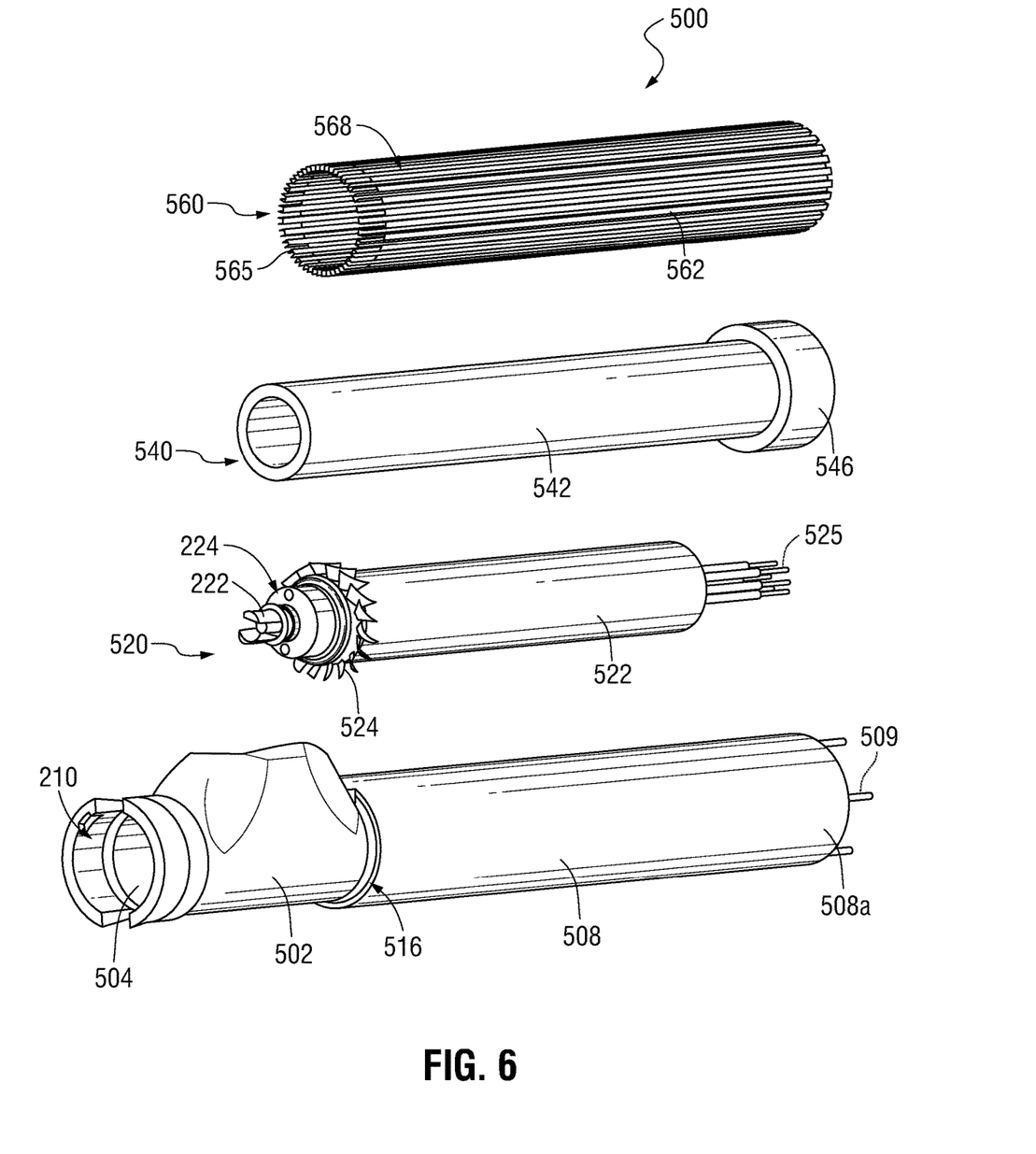
FIG. 6 is an exploded perspective view of the cooling assembly of FIG. 4 with parts separated.

Referring to FIGS. 4-6, cooling assembly 500 is operatively coupled with motor 224 (see FIG. 1) and defines handle housing 210 of handpiece assembly 200. In particular, cooling assembly 500 is configured to provide cooling to motor 224 of drive assembly 220. Cooling assembly 500 includes handle housing 210, a fan assembly 520, a heat transfer member 540, and a fin pack 560. With particular reference to FIG. 6, handle housing 210 defines a lumen 504 extending therethrough, and a slot 516 that serves as inlet or outlet of air. The handle housing 210 includes an adapter portion 502 configured to releasably engage proximal hub housing 110 of end effector assembly 100 and receive a portion of inner drive core 140 within lumen 504 thereof. The elongate cover 508 of handle housing 210 is configured to support motor 224 therein and to, e.g., concentrically, receive fan assembly 520, heat transfer member 540, and fin pack 560 therein. Distal drive rotor 222 extends distally from motor 224 into adapter portion 502 of handle housing 210 to facilitate engagement with inner drive core 140 upon engagement of end effector assembly 100 with handpiece assembly 200. Adapter portion 502 and elongate member 508 are separated by slot 516. Handle housing 210 further includes a plurality of fingers 509 extending proximally from a proximal portion 508a of elongate cover 508. Handle housing 210 may be formed as a single construct. In particular, handle housing 210 may be monolithically formed.

The fan assembly 520 includes a tubular member 522 dimensioned to receive at least a portion of motor 224 (see also FIG. 1), and a plurality of blades 524 rotatably supported on tubular member 522 such that the plurality of blades 524 extends radially outward from tubular member 522. The plurality of blades 524 is operatively coupled with distal drive shaft 222 of motor 224 for concomitant rotation therewith. Under such a configuration, fan assembly 520 may be actuated without additional actuation mechanism. In addition, actuation cables 525 extend through tubular member 522. Actuation cables 525 impart power and control signals from the control unit (not shown) to motor 224 via cable 230 to distal drive rotor 222. Fan assembly 520 is disposed within handle housing 210 such that the plurality of blades 524 is disposed adjacent slot 516 of handle housing 210, and tubular member 522 is in registration with elongate cover 508.

With continued reference to FIGS. 4-6, heat transfer member 540 includes a tubular portion 542 and an outer portion 546 extending distally from tubular portion 542. Heat transfer member 540 is thermally coupled with motor 224 (FIG. 1). Tubular portion 542 is supported about tubular member 522 of fan assembly 520 received within lumen 504 of handle housing 210. Outer portion 546 of heat transfer member 540 is disposed external to handle housing 210 such that fingers 509 engage outer portion 546 such that the outer portion 546 and handle housing 210 define an opening 511 to expose at least a portion of fin pack 560 and to serve as an air outlet for fan assembly 520.

With particular reference to FIG. 6, fin pack 560 is dimensioned to be supported on tubular portion 542 of heat transfer member 540. Fin pack 560 includes a tubular base 562 defining a lumen 565 therethrough, and a plurality of fins 568 circumferentially arranged about tubular base 562. Each fin 568 extends radially outward from tubular base 562 and along at least a portion of the length of tubular base 562. In particular, a portion of each fin 568 extends distally from tubular base 562 such that the plurality of fins 568 defines a gap with tubular portion 542 of heat transfer member 540 when fin pack 560 is supported about heat transfer member 540.

When fin pack 560 is mounted on tubular portion 542 of heat transfer member 540, heat generated by motor 224 (FIG. 1) is transferred to tubular member 522 of fan assembly 520, which is then, transferred to heat transfer member 540. Alternatively, tubular member 522 of fan assembly 520 may be thermally insulated from motor 224, and the heat transfer member 540 may be thermally coupled with motor 224. Heat transfer member 540 is thermally coupled with fin pack 560. When motor 224 is actuated, distal drive rotor 222 of motor 224 rotates the plurality of blades 524. In this manner, air is drawn through slot 516 of handle housing 210, across blades 524, and is advanced through an annular space between fin pack 560 and elongate cover 508, thereby facilitating heat transfer away from motor 224 and forced cooling thereof. The air then travels out of opening 511 defined by elongate cover 508 and outer portion 546 of heat transfer member 540. Is also contemplated that handle housing 210 may be an additional housing disposed about the handle housing of cooling assembly 500 and, in such embodiments, may define slots (not shown) in communication with slot 516 and opening 511 to facilitate dissipation of heat out of handle housing 210.

With brief reference back to FIG. 1, outflow tubing 240 is configured such that, with end effector assembly 100 engaged with handle housing 210, outflow tubing 240 communicates with the internal lumen of inner cutting shaft 130 of end effector assembly 100 to receive resected tissue as well as fluid and other debris withdrawn from an internal surgical site during use. Outflow tubing 240 is configured to ultimately connect to a collection canister (not shown) or other suitable collection reservoir for collecting the tissue, fluid, and debris withdrawn from the internal surgical site. Outflow tubing 240 may extend along and/or through handle housing 210 or may otherwise be associated therewith or separate therefrom.

In order to engage end effector assembly 100 with handpiece assembly 200, end effector assembly 100, led by inner drive core 140, is inserted into handle housing 210 of handpiece assembly 200. Upon further insertion of end effector assembly 100 into handpiece assembly 200, inner drive core 140 is slid about distal drive rotor 222 to thereby rotatably engage distal drive rotor 222 and inner drive core 140 with one another.

Once tissue resecting device 10 is assembled, e.g., once end effector assembly 100 is engaged with handpiece assembly 200 as detailed above, tissue resecting device 10 is ready for use. In use, tissue resecting device 10 is positioned within an internal body cavity or organ, e.g., a uterus, such that the distal end portion of end effector assembly 100 is positioned adjacent tissue to be removed. Tissue resecting device 10 may be inserted through an endoscope, e.g., a hysteroscope, or other device, or may be used independently.

Once tissue resecting device 10 is positioned adjacent tissue to be removed, tissue resecting device 10 is activated. Activation of tissue resecting device 10 drives motor 224 which rotationally drives drive rotor 222. Rotation of drive rotor 222, in turn, drives rotation of inner cutting shaft 130 relative to elongated outer shaft 120. At this time, cooling assembly 500 provides cooling to motor 224 via the rotation of the plurality of blades 524 of fan assembly 520, which establishes air flow along and about heat transfer member 540 and fin pack 560, thereby facilitating the removal of heat from motor 224. Activation of tissue resecting device 10 also serves to activate suction through outflow tubing 240, thereby applying suction through inner cutting shaft 130. With such suction applied, tissue is drawn through window 128 of elongated outer shaft 120 and window 138 of inner cutting shaft 130, while edge 129 and/or cutting blade 139 facilitates cutting of tissue as a result of the rotation of windows 128, 138 relative to one another. The suction also draws fluid and debris through inner cutting shaft 130. The tissue, fluid, and debris suctioned through inner cutting shaft 130 travel proximally through inner cutting shaft 130, inflow tubing 240, and ultimately, are deposited in a collection canister (not shown). Tissue resecting device 10 may be utilized until the desired tissue is removed from the internal body cavity or organ. Once the desired tissue is removed, tissue resecting device 10 may be deactivated and removed from the surgical site. Thereafter, end effector assembly 100 may be disengaged from handpiece assembly 200 and discarded (or sent for reprocessing), while handpiece assembly 200 is cleaned and/or sterilized for reuse.

As an alternative to handpiece assembly 200 configured for manual grasping and manipulation during use, tissue resecting devices 10 may alternatively be configured for use with a robotic surgical system wherein the end effector assembly 100 is configured to engage a robotic arm of the robotic surgical system in a similar manner as detailed above with respect to engagement of end effector assembly 100 with handpiece assembly 200. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely controls the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A handpiece assembly for use with a tissue resecting device comprising:
   a motor including a drive rotor; and
   a cooling assembly including:
      a housing including an adapter portion and an elongate cover extending proximally from the adapter portion, the housing defining a first slot between the adapter portion and the elongate cover;
      a fan assembly including a tubular member dimensioned to be received in the elongate cover of the housing, and a plurality of blades operatively coupled with the drive rotor of the motor for concomitant rotation therewith;
      a heat transfer member disposed about the tubular member of the fan assembly, the heat transfer member thermally coupled with the motor; and
      a fin pack including a tubular base supported about the heat transfer member, and a plurality of fins circumferentially arranged about the tubular base,
   wherein actuation of the motor advances air through a space between the elongate cover and the fin pack.

2. The handpiece assembly according to claim 1, wherein the heat transfer member includes an outer portion disposed external to the housing.

3. The handpiece assembly according to claim 2, wherein the housing and the outer portion of the heat transfer member define a second slot.

4. The handpiece assembly according to claim 3, wherein the housing further includes fingers extending distally from the elongate cover, the fingers engaging the outer portion of the heat transfer member to define the second slot.

5. The handpiece assembly according to claim 1, wherein at least one fin of the plurality of fins extends distally from the tubular base of the fin pack such that the at least one fin and the tubular member of the fan assembly define a gap.

6. The handpiece assembly according to claim 1, wherein the plurality of fins of the fin pack extends along a length of the tubular base.

7. The handpiece assembly according to claim 1, wherein the housing is formed of at least one of plastic or metal.

8. A handpiece assembly for use with a tissue resecting device comprising:
a motor; and
a cooling assembly including:
  a housing including an elongate cover defining a first lumen therethrough;
    a fan assembly including a tubular member configured to be received in the first lumen of the elongate cover of the housing, and a plurality of blades rotatably supported on the tubular member and operatively coupled with the motor for concomitant rotation therewith; and
    a fin pack including a tubular base and a plurality of fins extending radially outward from the tubular base, the tubular base disposed within the elongate cover and about the tubular member of the fan assembly,
  wherein actuation of the motor rotates the plurality of blades of the fan assembly to thereby advance air through a space between the fin pack and the elongate cover of the housing to facilitate cooling of the motor.

9. The handpiece assembly according to claim 8, wherein an outer portion of the fan assembly has an annular configuration.

10. The handpiece assembly according to claim 8, wherein the housing is formed of at least one of plastic or metal.

11. The handpiece assembly according to claim 8, wherein at least one fin of the plurality of fins of the fin pack extends distally from the tubular base.

12. The handpiece assembly according to claim 11, wherein the at least one fin of the plurality of fins of the fin pack defines a gap with the tubular member of the fan assembly.

13. The handpiece assembly according to claim 8, wherein the cooling assembly further includes a heat transfer member thermally coupled with the motor, the heat transfer member including a tubular portion configured to be supported about the tubular member of the fan assembly, and an outer portion extending distally from the tubular portion.

14. The handpiece assembly according to claim 13, wherein the tubular portion of the heat transfer member is disposed within the elongate cover of the housing, and the outer portion is external to the elongate cover.

15. The handpiece assembly according to claim 14, wherein the housing further includes fingers extending distally from the elongate cover such that when the tubular portion of the heat transfer member is received within the elongate cover, the outer portion of the heat transfer member engages the fingers and defines an opening configured to discharge air therethrough.

16. The handpiece assembly according to claim 14, wherein each fin of the fin pack extends at least the length of the tubular base.

17. The handpiece assembly according to claim 16, wherein at least a portion of each fin of the fin pack is in communication with the opening defined between the elongate cover and the outer portion of the heat transfer member.

18. The handpiece assembly according to claim 16, wherein at least one fin of the plurality of fins of the fin pack engages the outer portion of the heat transfer member such that the at least one fin is thermally coupled with the outer portion.

19. The handpiece assembly according to claim 16, wherein at least one fin of the plurality of fins of the fin pack is in communication with a slot defined between the elongate cover and an adapter portion of the housing.

* * * * *